（12） United States Patent
Ganton et al.

(10) Patent No.: US 11,850,046 B2
(45) Date of Patent: Dec. 26, 2023

(54) SYSTEM AND APPARATUS FOR ENABLING LOW POWER WIRELESS DEVICES

(71) Applicants: Robert Bruce Ganton, San Diego, CA (US); Robert S Ballam, Eaton Hill (CA)

(72) Inventors: Robert Bruce Ganton, San Diego, CA (US); Robert S Ballam, Eaton Hill (CA)

( * ) Notice: Subject to any disclaimer, the term of this patent is extended or adjusted under 35 U.S.C. 154(b) by 99 days.

(21) Appl. No.: 17/187,798

(22) Filed: Feb. 27, 2021

(65) Prior Publication Data

US 2022/0007974 A1 Jan. 13, 2022

Related U.S. Application Data

(60) Provisional application No. 62/982,468, filed on Feb. 27, 2020.

(51) Int. Cl.
*H03F 3/45* (2006.01)
*A61B 5/145* (2006.01)
*A61B 5/00* (2006.01)

(52) U.S. Cl.
CPC ........ *A61B 5/14532* (2013.01); *A61B 5/0002* (2013.01)

(58) Field of Classification Search
CPC .......................................................... H03F 3/45
USPC .......................................... 330/10, 260, 261
See application file for complete search history.

(56) References Cited

U.S. PATENT DOCUMENTS

| | | | | |
|---|---|---|---|---|
| 3,920,284 A * | 11/1975 | Lane | ................ | B60T 8/885 303/159 |
| 5,241,282 A * | 8/1993 | Poole | ................ | H03G 7/001 327/330 |
| 5,625,698 A * | 4/1997 | Barbetta | ................ | H04R 3/002 381/59 |
| 7,554,412 B2 * | 6/2009 | Kojima | ................ | H03L 7/087 331/11 |
| 9,274,145 B2 * | 3/2016 | Goeke | ................ | H03F 3/45475 |

* cited by examiner

*Primary Examiner* — Henry Choe (57) ABSTRACT

A simplified electronics approach to allow cost, size, and power consumption to be reduced while maintaining state of the art accuracy and reliability, key features for wireless medical devices/systems. Extreme accuracy is achieved by innovative noise shaping and filtering introduced to the electrochemical sensor, before sampling by the analog to digital converter. Introduction of the noise to the electrochemical sensor provides very low power biasing which is necessary to achieve overall reliable and very accurate bias for the electrochemical reaction cell.

10 Claims, 7 Drawing Sheets

PRIOR ART

SYSTEM AND APPARATUS FOR ENABLING LOW POWER WIRELESS DEVICES

RELATED APPLICATIONS

This application claims priority to U.S. provisional patent application No. 62/982,468, filed Feb. 27, 2020, and entitled "System and Apparatus for Enabling Low Power Wireless Devices," which is incorporated herein in its entirety.

FIELD OF THE INVENTION

The field of the present inventions is electronic circuitry for providing a high-quality voltage reference signal, for example, to an operational amplifier. An embodiment of the new circuitry was designed with medical devices in mind to reduce power consumption while maintaining high accuracy of data collected from measurements taken from one or more sensors. The new circuitry can be used across a wider spectrum of devices that also benefit from a low cost and low power consumption reference signal and may be particularly useful for devices with disposable or rechargeable batteries in mind. Other applications for this new circuitry would be the gas/oil mining and refining/exploration industries, or research facilities involving volcanic and tectonic areas. Any device that uses an electronic sensor to measure current that presently uses a discrete and high precision bias reference component could benefit from the new circuitry.

BACKGROUND

Continuous Glucose Monitors (CGM) have been in existence for some time, however it has been difficult for them to attain widespread and ubiquitous use as the cost and size have been prohibitive. In order to achieve high accuracy of the measurements produced by CGMs, it is customary for the electronics design of the CGM to use high accuracy references which provide a stable measurement and bias source for driving an electrochemical reaction. The design typically incorporates a highly accurate analog to digital converter (ADC). Additionally, some CGMs have Application Specific Integrated Circuits (ASIC) with specialized circuits that include references, and an embedded Digital Signal Processor (DSP) in an attempt to produce a circuit design with highly accurate measurements. The data from the electrochemical reaction are produced under the presence of a bias voltage generated by the ASIC and DSP. The resulting data is a current that is at a rate proportional, or nearly proportional, to the glucose content in the sampled tissue. The exact transform is dependent on the construction of the sensor elements performing the electrochemical reaction.

The circuit in a CGM with ASIC and DSP components are manufactured with costly components that are not necessary for the continued use of CGMs to maintain highly accurate measurements. The circuit in a CGM must maintain, monitor and measure a bias voltage and resulting current flow. The medical market demands are such that a circuit that can maintain, monitor and measure a bias voltage and resulting current flow, while using as little current as possible and with a high degree of fidelity, can stimulate innovative ways to improve the design to achieve low current consumption. The total cost of CGM devices per patient per year is determined by the replacement cost of the device and the length of time a device can operate at the required accuracy. A design which uses a lower energy consumption rate, which is typically corresponding with a lower current consumption, has the advantage that it can be lower cost and thus meet market cost target requirements. In addition to achieving low cost targets, the device must also meet small size requirements for patient comfort and convenience. The low current consumption can produce a device that is a smaller size, and the smaller size allows for a more comfortable sensor solution. The sterile nature of the design motivates the device to be disposable. Having a disposable medical device with low power consumption allows for the use of low cost coin cell or printed battery, further improving the metrics of the design. The innovative embodiment presented in the Description below provides a solution to meet the market demands.

SUMMARY

Various embodiments of the new circuitry provide an electrochemical sensor with a high quality and inexpensive reference bias voltage for the sensor to analyze data collected from various elements, such as environmental factors or biological factors. This new circuity is constructed from inexpensive, readily available, and easy to assemble components, thereby eliminating the need for an expensive high performance voltage reference components. By eliminating the costly discrete Application Specific Integrated Circuits (ASIC) and Digital Signal Processor (DSP) components typically used to generate a reference voltage, and providing the sensor with a reference bias voltage generated from within the new circuit itself, the newly designed embodiments provide a low cost, low power solution to medical devices thus providing greater global access to medical technology necessary for patients requiring highly accurate tissue analysis to potential life threatening conditions.

Generally, the new circuit generates a driving signal that can be considered analogous to noise, for example by using one or more pulse wave modulators, and analog to digital convertor and a resistor/capacitor network. The driving noise produced from within the circuit itself is generated from one or more resistor/capacitor network(s) (RC), as well as an additional analog to digital converter, designed into the circuit to provide a bias voltage reference to the sensor. By shaping and filtering the driving noise to desirable levels to meet industry standards for the sensor and applicable conditions, highly accurate data measurements by the sensor are maintained, while reducing power consumption. The RC networks that produce the driving noise may be regulated and adjusted using a software platform to control the on/off states of parts of the circuit to further reduce power consumption while maintaining the quality of the reference voltage.

BRIEF DESCRIPTION OF THE DRAWINGS

The accompanying drawings serve to aid the detailed description (with the exception of FIG. 1 which is prior art) of the invention given below and are provided solely for the illustration of the embodiment and not limitation thereof.

DETAILED DESCRIPTION

The various embodiments will be described with respect to the accompanying drawings. The ensuing description provides embodiment(s) only, and is not intended to limit the scope, applicability or configuration of the disclosure or the claims.

The term "sensor" is used herein to refer to a device that detects or measures a physical property of a substance and generates signals, or otherwise responds to the physical property. The sensor may be any electrochemical sensor such as, and not limited to, those used to measure tissue samples containing glucose, and/or other analytes or substances, and refer the analyzed content of the tissue samples to a resulting current flow. The signals generated by the sensor may be analyzed by a microcontroller to measure the one or more detectable substances based on a correlation between the signal and the underlying quantity of the detectable substances. For example, some detectable substances such as, and not limited to, biological factors with clinical applications, such as glucose in sampled live human tissue, or for certain atmospheric factors, such as toxic gases in sampled atmospheres surrounding volcanoes or mining sites, etc.

The term "logic system" is used herein to refer to a system of digital logic circuitry designed to perform a function to control the generation of custom-tailored pulses of signal in order to generate a waveform which has long term predicable average values. In one embodiment, the logic system can be used by the system of RC networks to charge the capacitor with minimal microprocessor involvement.

The term "software platform/algorithm" is the combination of the embedded software and measurement algorithms such that the software platform/algorithm can implement measurement methods with the accompanying digital system.

The term "microcontroller or processor" is used herein to refer to anyone or all of a general-purpose processor, conventional processor, controller, FPGA, state machine, or combinations. The embodiment may be a microprocessor comprised within a System on Chip (SoC), connected internally to peripherals such as timers, output compare blocks, Analog to Digital Converters (ADCs), embedded memory, and interrupt controllers.

The term "drive noise" is, unless otherwise stated, used herein to refer to electrical signals produced within the circuit by resistor/capacitor network(s) and presented to an operational amplifier (OPAMP), which may be in the SOC. Although noise is traditionally considered undesirable in an electrical circuit, the various embodiments utilize the inventive drive noise for a beneficial effect for improving accuracy of the data collected by the sensor and reducing overall power consumption of the circuit.

Figure 1:
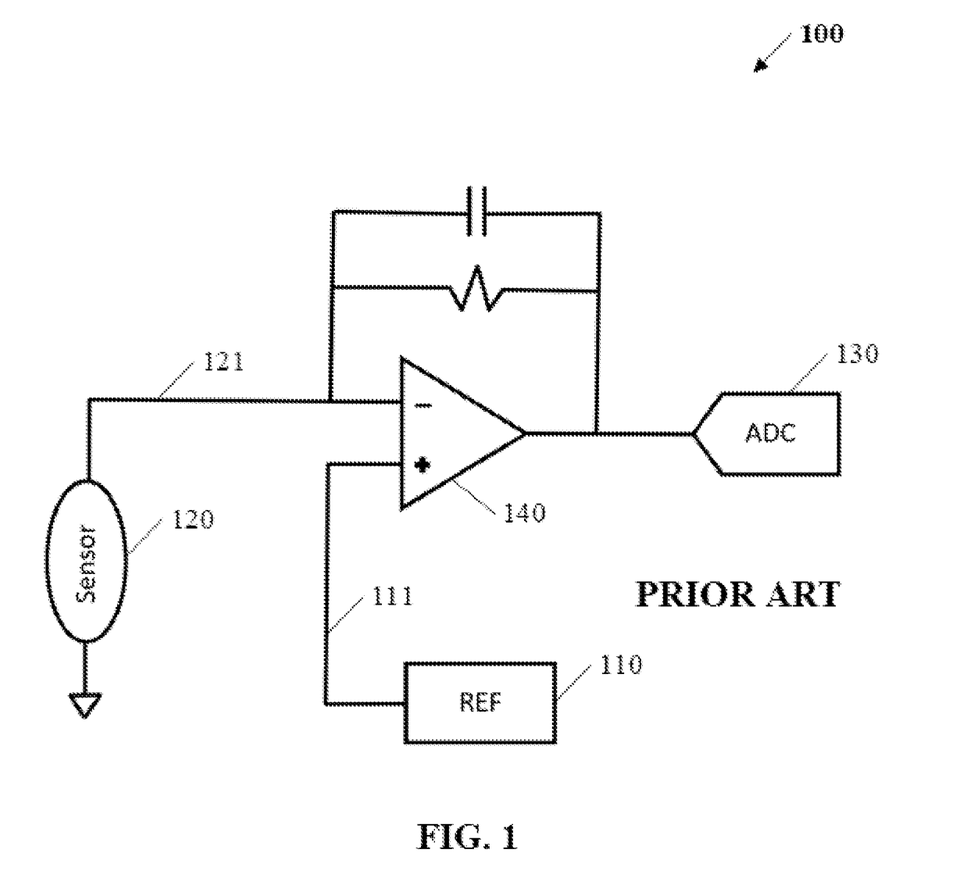
FIG. 1 illustrates a traditional prior art circuit with bias voltage provided by a discrete high performance reference component.

FIG. 1 is an example of a typical prior art circuit design 100 in use currently on Continuous Glucose Monitors (CGM). FIG. 1 is an example of a circuit using an outside discrete/dedicated reference voltage generating component 110, providing a reference bias voltage 111 for the op amp 140. Component 110 is an expensive high precision component, which the inventive new circuity, discussed with reference to FIG. 2, advantageously eliminates. A sensor input signal 121 is provided from the sensor 120, which is one input to op amp 140, while the reference bias voltage 111 is the other input to op amp 140. FIG. 1 is considered a typical design and is well known in the art.

Figure 2:
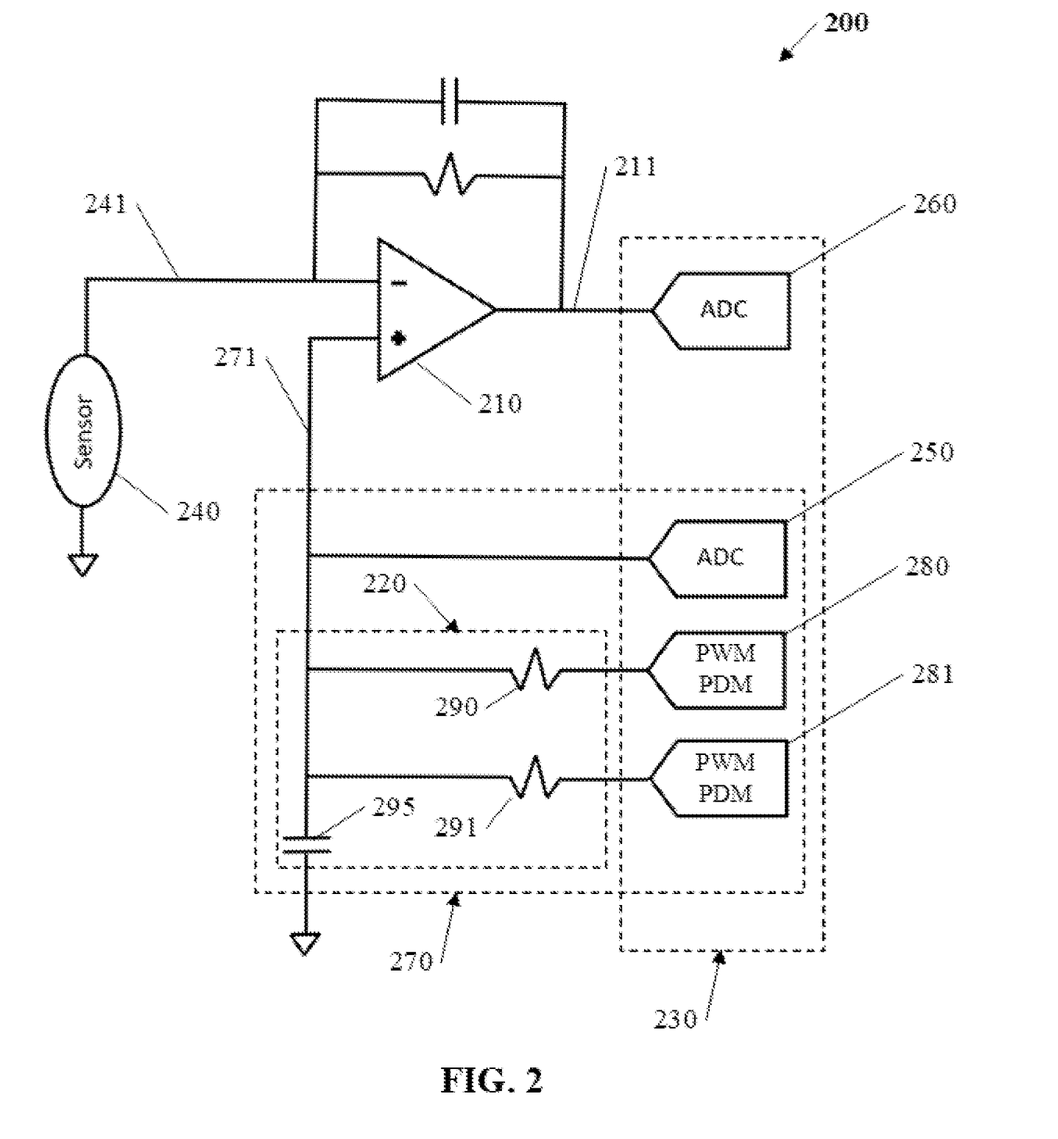
FIG. 2 illustrates an embodiment of the new circuit design with two resistor capacitor networks and an additional analog to digital converter, which together generate the reference voltage and drive noise signal required for the analog to digital signal sampling. The drawing illustrates the use of two resistor capacitor networks and is not meant to be limiting.

FIG. 2 illustrates a sensor circuit 200 incorporating an embodiment of the inventive new circuit. Generally, sub-systems 270 replace the expensive outside reference component 110 of FIG. 1. Sensor 240 is similar to known sensor 120, op amp 210 is similar to known op amp 140, and ADC 260 is similar to known ADC 130. Accordingly, these components will not be discussed in detail. Generally, sensor circuit 200 has an SoC 230 that has several electronic components, as well as a processor. It will be understood that some components illustrated as being in the SoC 230 may be provided as discrete components, and some components illustrated as discrete components may be provided within the SoC 230, as is well understood in the art.

Generally, the sensor 240, such as a the wires used for a CGM device, provides an input signal 241 to one input (−) of op amp 210. The input signal 241, for example, may provide a current signal that is indicative of the level of glucose detected by sensor 240. A noise drive signal 271 is provided from subsystems 270, which eliminate the need for any expensive high precision voltage reference component. The noise drive signal 271 is received as the second input (+) to the op amp 210. The op amp 210 outputs a sample signal 211, which is received by an ADC 260 in the SoC 230.

The sub-systems 270 of FIG. 2 may provide the reference bias drive noise signal 271 as a voltage or current, and using the processor in the SoC 230 can apply signal processing mathematics to produce a highly accurate signal, with minimal cost and power draw. The disclosed embodiment shown in FIG. 2 can be viewed as three parts working together: (1) bias voltage 271 generation for the sensor 240 without use of an expensive high performance reference voltage component; (2) current measurement of sample line 211 to digital conversion with ADC 260; and (3) low power control modes in the SoC to achieve overall low power consumption of the device.

Although bias voltage generation is traditionally considered constant, in the present embodiment it can be both flexible and constant meaning that it can hold the reference bias constant or vary the bias due to environmental effects or in the case of medical sensors, as a result of biological and/or physiological effects with the net effect producing a high-quality bias voltage and a lower power profile. Although power consumption is a complicated field, it is generally considered that the longer a circuit consumes current, the higher the average current consumption. Also, the more current a device, or its subsystem, consumes, the higher the average current consumption. Since energy used is proportional to current consumption multiplied by voltage of system, or subsystem, multiplied by time in operation, the current embodiment of a dual RC network 220 produces an overall energy consumption rate that is lower than the overall energy consumption rate for a single RC network. By way of example, a single RC time constant network would need 47 ms to meet accuracy and stability requirements, and a dual RC time constant network in the current embodiment would be 470 us and 47 ms. In various embodiments with a dual RC network 220, the final stable state is achieved much quicker, and with less energy consumed than in the single RC time constant design.

An example of a single RC pulse width modulator (PWM) circuit with a time constant of 47 ms would require 0.235 s to stabilize for an error rate of less than 1% error from target value. In a RC PWM circuit with a time constant of 470 us, it would take less than 2.35 ms to stabilize to less than 1% error. Once stabilized, the system would switch to using the 47 ms time constant RC circuit for maintenance. Switching RC networks can represent a savings of almost 100× improvement of the power draw on the subsystems over the single PWM method.

In order to achieve significant performance improvements over current state-of-the-art methods, which use an expensive high performance voltage reference 110 to achieve bias voltage generation, two different techniques are presented, and both represent significant improvements in both energy consumption rate and agility, that is the ability to generate a flexible output voltage or a range of voltages, in the total performance over current methods. Current known methods using a voltage reference to generate the bias voltage require approximately 5 uA continuously and provide no ability to vary the output voltage. In all embodiments disclosed herein there are significant portions of time where the subsystem(s) 270 can be powered off by the processor, and the subsystem circuit 270 can operate at near zero power. Powering off the subsystems 270 for significant portions of time directly impacts and benefits the overall energy consumption rate.

In method 1 (not shown on FIG. 2), the SoC 230 provides a single PWM or a pulse density modulator (PDM) channel 280 to a single resistor 290 capacitor 295 (RC) network. The PWM/PDM signal, resistor 290, and capacitor 295 work together to create an analog voltage, which ultimately produces the bias drive noise voltage 271. In method 2 (illustrated in FIG. 2), the Soc generates two separate PWMs 280/281 (in this document PWM and PDM can be used interchangeably for this application), with two separate RC 220 paths: (1) PWM/PDM 280 coupled to resistor 290/capacitor 295 and (2) PWM/PDM 281 coupled to resistor 291/capacitor 295. One of these RC networks is constructed to be a higher time constant RC network, while the other is constructed to be a lower time constant RC network. The output from the RC paths connect to the positive side of a low bias OPAMP 210 as the drive noise voltage 271. The higher time constant RC network is used for long term maintenance of the bias voltage and has a lower noise profile than the lower time constant based PWM bias voltage generation. Generally, a higher time constant RC network will have a similar duty cycle, with smaller ripple voltage, so less noise is generated. In contrast, a lower time constant RC network will have a similar duty cycle, that will generate a higher level of ripple and noise. The use of two PWMs is not necessary and is not intended to be limiting. In fact, more or fewer could be used to achieve similar goals, but use of two PWM's has been shown to be an advantageous number when using a traditional PWM system to drive RC networks 220. Additionally, the sensor system 200 could use any logic system such as a digital circuit contrived to produce a predictable signal with a specific average output level over a reasonably short time such as the PWM, with similar results.

It will be understood that SoC 230 has a processor, such as a microprocessor, that is used to control various components, such as ADC 260, ADC 250, PWM/PDM 280 and PWM/PDM 281. The microprocessor may also operate algorithm processes, evaluate the detected levels of glucose, and generate messages to internal and external devices.

By way of example, sensor circuit 200 may use the following component values. It will be understood that many other combinations can be substituted within the spirit of the claimed invention.

RC Network 1 (higher time constant) 470 us
PWM/PDM 280 16 MHz at 18.333% ON duty cycle
R290: 470 ohms
C295 1 uF
RC Network 2 (lower time constant)
PWM/PDM 281 47 ms 16 MkHz at 18.3333%
R291: 47000 ohms
C295 1 uF For both methods disclosed with reference to FIG. 2, the drive noise voltage 271 will vary over time, which can aid the current measurement to digital conversion from sample line 211 as discussed below. The varying voltage 271 over time achieves two key goals. Firstly, the system 200 can achieve very fast stabilization of the measurement and bias generation circuitry through the use of a low time constant RC network. This low time constant RC network allows the output of the PWM to have a predictable adjustment time at the positive input of the OPAMP 210. Additionally, various embodiments can have a high value time constant RC network to allow low power maintenance and provide fine adjustment of the overall bias voltage to levels which cannot easily be attained by a single RC network being driven by a standard or traditional low power PWM system. The embodiment can achieve three goals simultaneously which are difficult or expensive to achieve when designing the system with outside reference biasing 110. The three characteristics are (1) agile voltage bias generation, (2) quick settling time to achieve target voltage, and (3) the ability to go to low power mode and therefore turn off the PWM circuit/system 270 to save power for extended periods of time. These three characteristics result with the embodiment having very low power consumption. Other designs may try to achieve this by turning off the Bluetooth or wireless function entirely during times when it is not active, which would require an additional microcontroller to manage the measurements, ultimately impacting size and cost.

Figure 3:
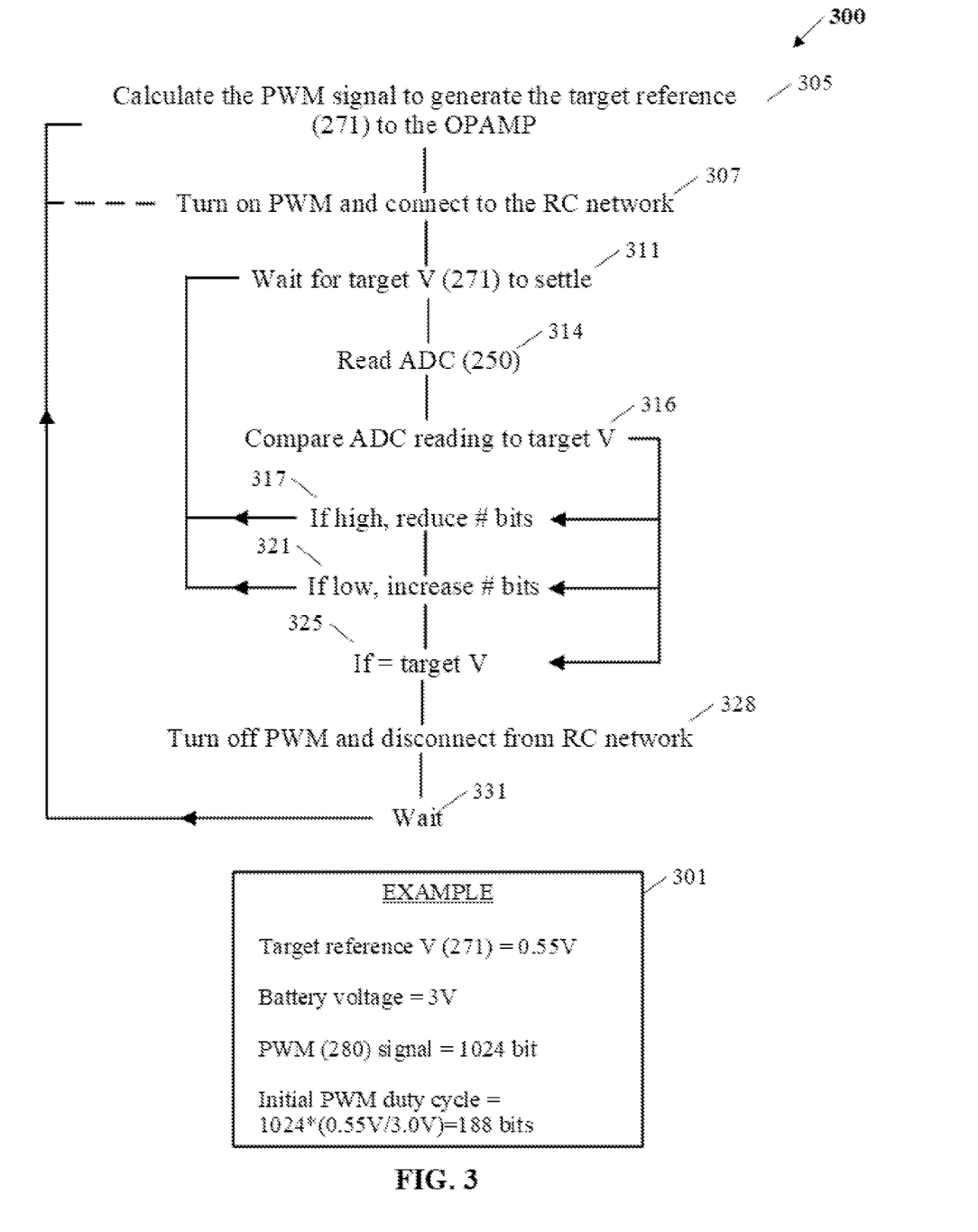
FIG. 3 is a flowchart of a process for controlling the new circuit design to generate a reference voltage using a single RC network.

Referring now to FIG. 3, a method 300 for generating a reference voltage is illustrated. Method 300 uses a single RC network. In this example, it is desired to set the reference voltage 271 at 0.55 volts, as shown in example box 301. It will be understood that other operational amplifiers or other electrochemical sensors may require higher or lower voltages. By way of further example, the PWM is a 1024-bit generator, and the battery output is 3 volts. It will be understood that the battery voltage may be assumed to be 3 volts, and in other cases it may be desirable to measure the battery voltage in case there has been a drain on the battery. However, if the battery voltage is measured or assumed to be 3 volts, then the PWM duty cycle is equal to 0.55 volts divided by 3.0 volts, multiplied by 1024 bits. This results in the initial setting for the PWM to be 188 bits. (188 bit Duty cycle=(0.55V/3.0V)*1024 bits.) in this way the initial duty cycle of 188 bits is calculated at block 305. In block 307, the PWM is powered up and connected to an RC network. As illustrated in block 311, the system waits for the voltage on reference line 271 to settle. At that time, ADC 250 samples the voltage reference line 271 and then in block 316 the sampled measurement is compared to the target voltage. If the actual reading is higher than the target voltage 317, then the number of bits is reduced, for example to 187, and the system goes back to wait for the new voltage to settle on line 271. If the actual reading is lower then the target voltage 321, then the number of this is increased, for example to 189, and the system goes back to wait for the new voltage to settle on line 271. If the actual reading is sufficiently close to the target value 325, then the PWM is powered off and disconnected from the RC network as shown in block 328. The system has now entered a low power mode, so will wait 331 a period of time before reactivating the system. It will be understood that this amount of wait time can be derived from experimental data, or may be calculated according to the time constant of the RC network. After the system turns back on, it may optionally go back and just turn the PWM back on and connect to the RC network as shown in block 307. However, it may be preferable to measure the battery voltage and then recalculate the PWM signal as shown in block 305.

Additionally, this method will leave some residual error in the generation of the bias voltage. This error may be acceptable in some applications and may not be acceptable in some other applications. In the scenario where it is not acceptable the following additional flow chart explains how to improve accuracy by using a second PWM channel with a longer time constant Referring now to FIG. 4, a method 400 for generating a reference voltage is illustrated. Method 400 uses two RC networks. It will be understood that three or more RC networks may be used for specific applications and to provide particular qualities for the reference voltage. In this example, it is desired to set the reference voltage 271 at 0.55 volts, as shown in example box 401. It will be understood that other operational amplifiers or other electrochemical sensors may require higher or lower voltages. By way of further example, the PWM is a 1024-bit generator, and the battery output is 3 volts. It will be understood that the battery voltage may be assumed to be 3 volts, and in other cases it may be desirable to measure the battery voltage in case there has been a drain on the battery. However, if the battery voltage is measured or assumed to be 3 volts, then the PWM duty cycle is equal to 0.55 volts divided by 3.0 volts, multiplied by 1024 bits. This results in the initial setting for the PWM to be 188 bits. (188 bit Duty cycle=(0.55V/3.0V) *1024 bits.) in this way the initial duty cycle of 188 bits is calculated at block 305. In block 307, the PWM is powered up and connected to the first RC network. For this example, the time constant of PWM channel 1 is 10 ms and that the time constant of PWM channel 2 is 10 s. As illustrated in block 411, the system waits for the voltage on reference line 271 to settle. The system will wait for the reference line 271 to settle, which is calculated based upon the time constant of the first RC network. Here the wait time may be set to be 10 times the time constant of the first RC network. It will be understood that other wait factors may be used. Since the first RC network has a time constant of 10 ms, in this example the system would wait 100 milliseconds as shown in block 411, and then turn off the first PWM 280 and disconnect the first RC network as shown in block 416. By having the first RC network have a relatively short time constant, the reference voltage will be very quickly brought to be near the target voltage. Now that the first PWM280 and the first RC network have been disconnected, the method 400 will turn on the second PWM 281 and connect the 2nd RC network as illustrated at block 421.

Figure 4:
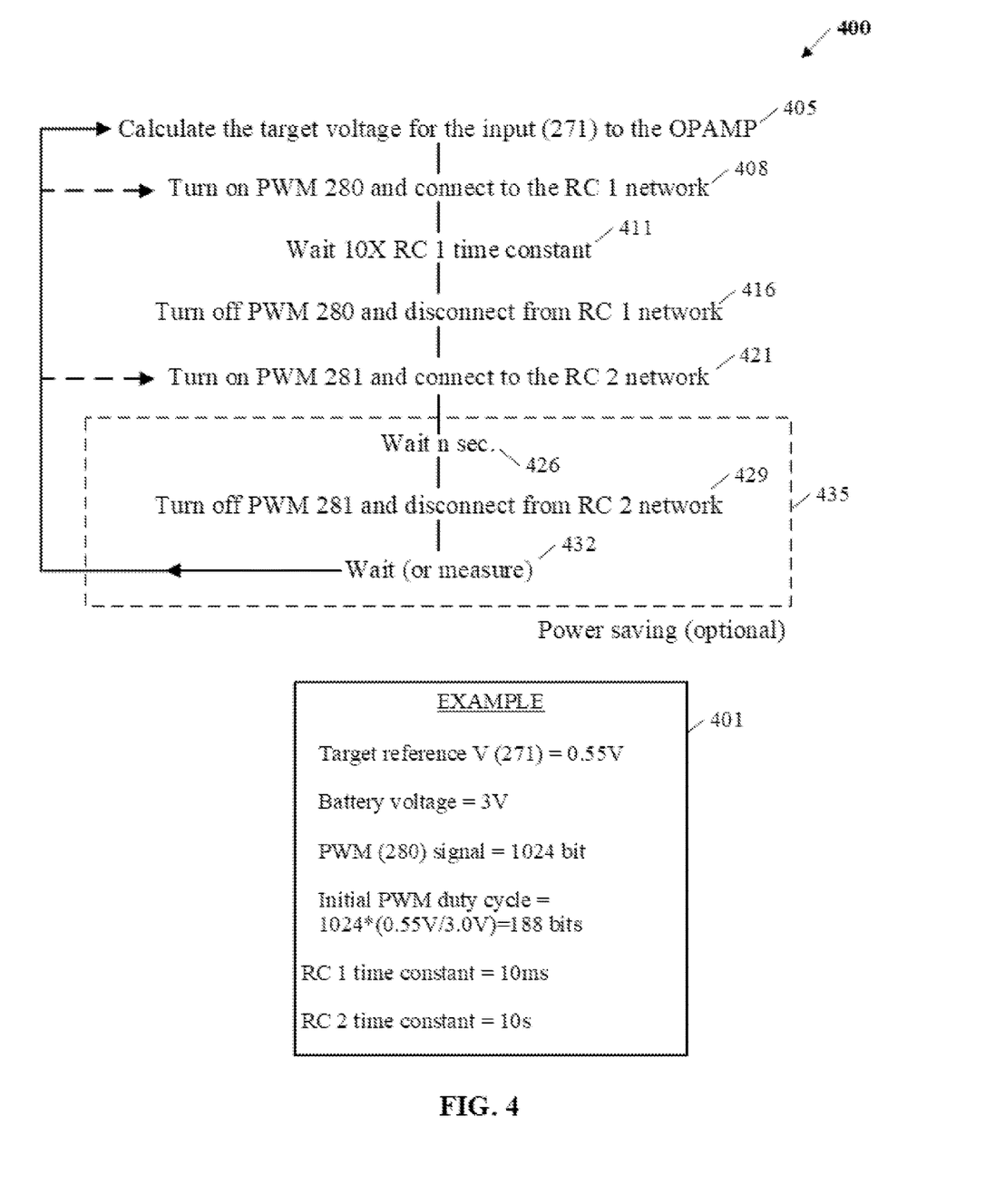
FIG. 4 is a flowchart of a process for controlling the new circuit design to generate a reference voltage using two RC networks.

At this point the method 400 could maintain the reference voltage with the PWM 281 and the second RC network running constantly due to the long time constant of the second RC network, this circuit would advantageously draw less power, however, additional power savings may be had using the power saving mode 435. The system will wait a set number of seconds to assure that the second RC circuit has set the reference voltage 271 to the target voltage, as shown at block 426. In one example, this wait time may be set to the time constant of the 2nd RC network, which is 10 seconds. It will be understood that other times may be used. After the wait time has elapsed, then the method 400 turns off the PWM 281 and disconnects the second RC network as illustrated in block 429. The system is now in a power saving mode, as the PWM generators are both off, and both RC networks have been disconnected from the ASIC, such that capacitance losses are very much reduced, or even eliminated in this way, the system may leave the PWM generators off for a period of time as shown in block 432. This again maybe for a defined period of time, or there may be a measurement process that sets a threshold to turn the system back on. Once this time has elapsed, or the voltage 271 has dropped to a threshold point, then the system will reactivate. In one example the method 400 completely restarts, allowing the system to measure the battery and recalculate the initial number of bits for PWM280. In other cases, the system may just restart PWM 280 as shown in block 408, or other times may just turn on PWM 281 as shown in block 421

The advantage of using the PWM281 is two fold, it allows for a relatively lengthy delay from setting the PWM280 and Vtarget being achieved with very high accuracy such that it can be then disabled for power savings as compared to the PWM1 signal. PWM1 is used as it quickly, without undue delay, gets the Vtarget close to the goal value. By using both PWM1 and PWM2 with different RC time constant values, we can achieve optimally quick response time and achieve ideal accuracy with the lowest cost and lowest power.

Another embodiment is to use a combination of the first and second flow chart to achieve optimal accuracy and minimal power consumption.

Agile bias generation is useful to dynamically adjust to electrochemical variations over time and over the environmental variations which are typically encountered on a patient during the useful life of a medical monitoring device. These adjustments can be made during the device's operational time to a very fine level of precision based on both environmental measurements and electrochemical cues. Adjustments to the electrochemical and environmental variations are made through a software platform included with the embodiment, however initial calibration is made during manufacturing, releasing the patient of the necessity of calibrating the device upon purchase.

Surprisingly, the use of the low cost RC network(s) 220 to produce intentional noise on drive signal 271 can achieve higher accuracy data than a traditional ADC sampling technique. As noise is adjustable and intentionally present on noise drive signal 271, a resulting noise will also be generated by the op amp 210 and output on sample line 211. By using ADC 260 to sample the sample line 211, and averaging the results, a more accurate measurement may be obtained. As is well known, all ADC's have a quantization error due to the set number of digital steps an ADC can output. For example, an 8-bit ADC has 256 quantization steps, and if the measured value falls between any step, the ADC will select either the next higher or next lower step to report as the result. With this known ADC measurement process, the only way to achieve a more accurate result is use an ADC with more bits and quantization steps, which of course, adds expense and complexity to the overall circuit. The present control process enables a much more accurate result from any ADC by reducing quantization errors.

Figure 5A:
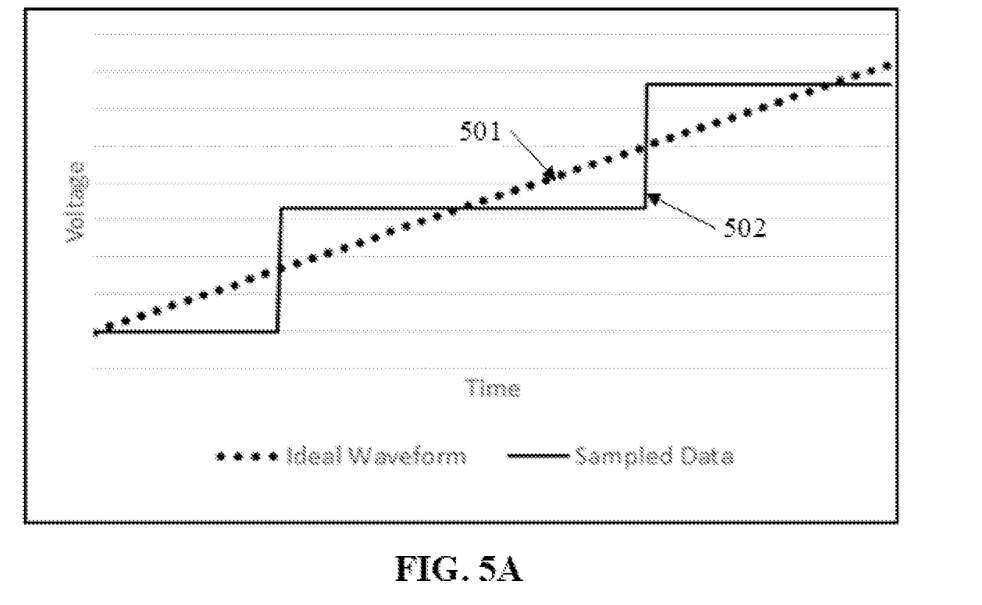
FIG. 5A illustrates a graph comparing the quantization error/noise introduced by the new circuit's sampling process compared to an ideal waveform that represents the ideal current input for the sensor.
Figure 5B:
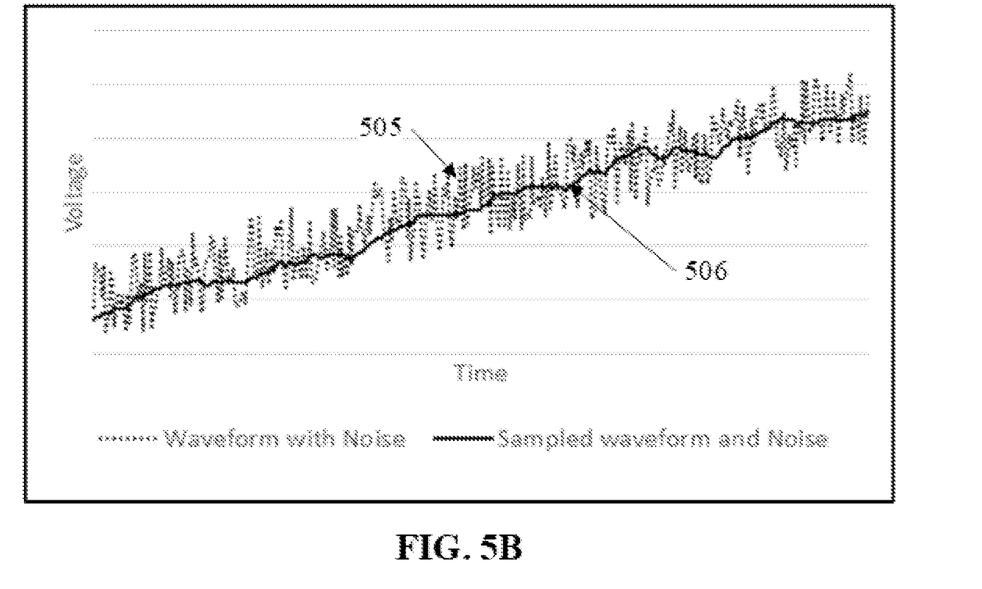
FIG. 5B illustrates a graph comparing a waveform of the measured signal with noise compared to the waveform of the enhanced ADC output with noise shaping and filtering.
Figure 5C:
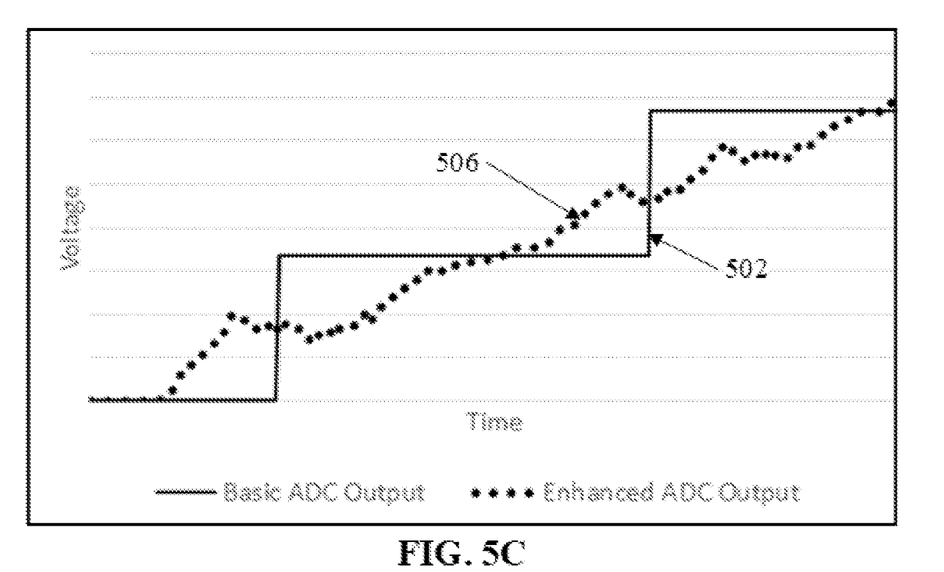
FIG. 5C illustrates a graph comparing the difference between the basic ADC sampled data with no noise shaping or filtering and the enhanced ADC output with noise shaping and filtering.

FIGS. 5A-C illustrate the improvement in accuracy by the intentional introduction of noise onto the noise drive line 271 and output sample line 211. FIG. 5A illustrates an output voltage 501 from an op amp that has almost no noise, such as would be present using known sensors. ADC measurements 502 show the measurement results from the ADC. As illustrated, the output 501 is rising nearly linearly, but due to quantization errors, the ADC will report "1" for a period time, the "2" for a period of time, and then "3" for a period of time. In this way, the accuracy of the measurement reported by the ADC is limited by the number of bits and quantization steps available. Accordingly, such a system would require a higher precision ADC.

In contrast, FIG. 5B shows the measurement results 505 of ADC 260 sampling the intentionally noisy output line 211. Due to the noise, the measurements appear far more erratic, depending on whether there is a positive or negative noise voltage on the output signal 211. These measurements are averaged, for example over some time period, and with the result being measurement 506. As summarized in FIG. 5C, when the output line from an op amp is rising linearly, if the output is relatively noise free, the ADC will report readings 502 with a huge quantization error. However, if the output line has intentional noise, and ADC readings are averaged, the results 506 will much more closely reflect the true output of the op amp. In this way, the addition of intentional noise enables the use of a lower cost and lower precision ADC, while giving better accuracy.

Figure 6:
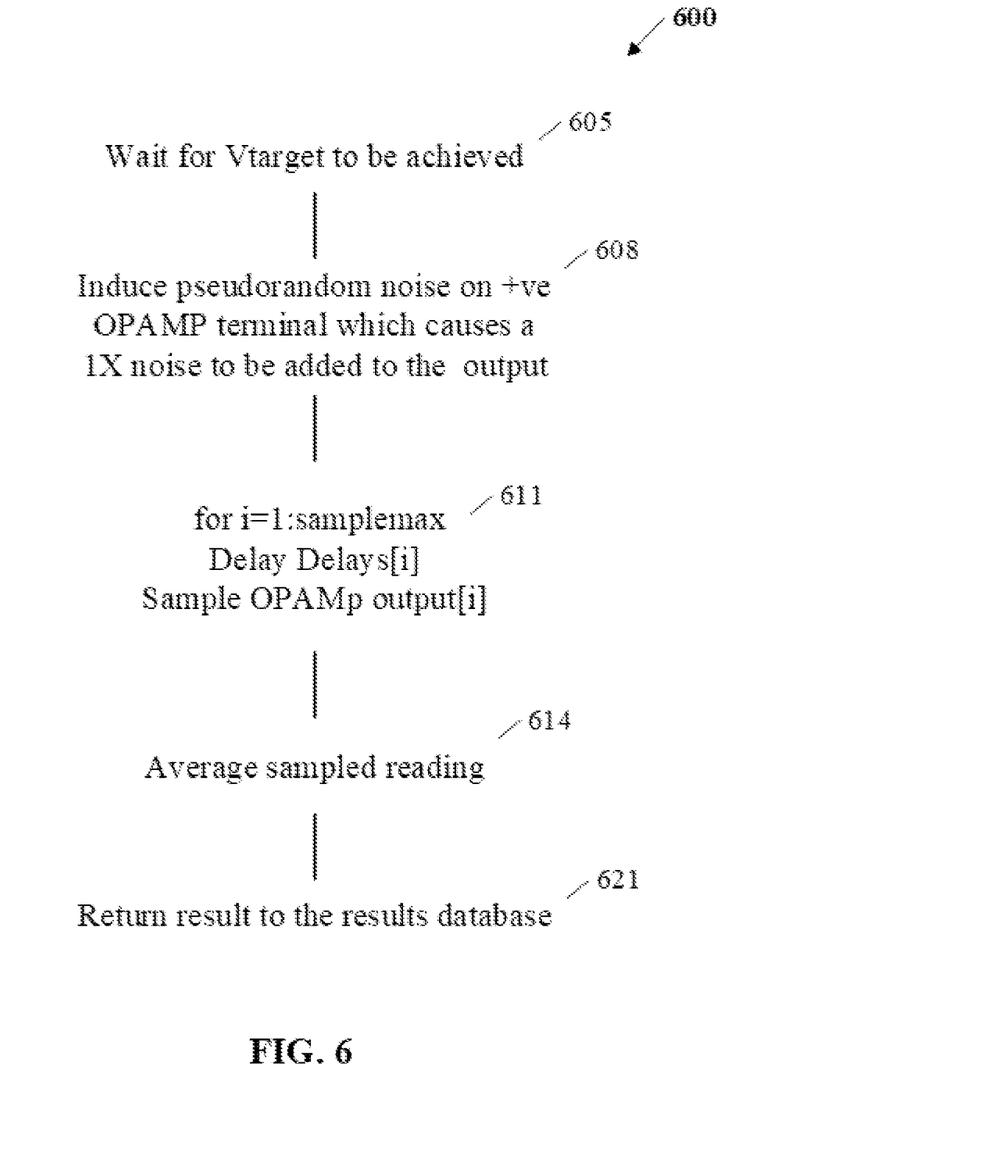
FIG. 6 is a flowchart of a process for measuring the output line for an OPAMP in accordance with the present invention.

This scheme of generating noise and sampling seems simple, but it allows the noise inherent in the system to be spread over time and thus reduced. So overall averaging of a signal which is gaussian in nature will achieve a 1/sqrt(n) reduction in noise. By adapting it to sample over a longer than necessary time allows short time transient effects in the system (such as muscle induced electrical noise, or outside electrical noise such has high frequency lamps or similar) can be reduced as it will have an effect over a small number of the samples and thus have a diminished effect on the overall reading. As illustrated in FIG. 6, this method 600 for improved measurement accuracy starts with waiting for the reference voltage 271 to settle as shown in block 605. While the average voltage of the target is achieved, there is a small level of residual noise included in the OPAMP+terminal.

At this point a pseudorandom noise is generated on at input to the op amp, which causes a known amount of noise to be generated at the output line to the opamp It will be appreciated that the level of noise on the output may be adjusted according to the amount of noise that is input in block 608. The noise added to the +ve terminal will be processed by the opamp and added directly to the output line of the OPAMP. This noise as it is generated by the PWM/PDM signal is pseudonoise in that its source is not random. By sampling the signal with the pseudonoise added, it allows the quantization noise and other external noise factors to be diminished by controlling sampling interval and rate to best effect. Although "pseudorandom" is often limited to a sequence of numbers or any digital data which satisfies one or more tests for randomness as used in method 600, a PDM/PWM signal as used here would generate a true PSEUDORANDOM noise. In method 600, adjusting the timing of the sampling to not be related to or synchronized with the PWM signal generation allows for a better pseudonoise signal to be generated.

As illustrated in block 611 an ADC is used to sample the output line. These sampled results are then averaged as shown in block 614, and then the results used as shown in block 621

The removal of the outside bias reference 110 and replacing it with the RC networks 220 and an ADC 250 subsystem in the circuit, as seen in FIG. 2, a more accurate value is achieved at a much lower cost and size. The added subsystems 270 to the circuit as shown in FIG. 2 allow the noise to be introduced onto the electrochemical sensor 240, and therefore the measurement to be at a rate which is not affected by the overall electrochemistry, while still allowing the sampling to be performed in a way to achieve a very accurate result, with approximately 17 bits of precision. By adding noise to the system which is larger than the quantization noise of the SoC ADC 260, the system can perform statistical calculations on the samples to achieve a higher precision result than could be achieved using direct SoC ADC 260 usage. As it is well known in the art that ADCs are limited to measuring integer values of voltage or current, the ADC 250 can measure the added noise to the system as a non-integer. For example, instead of a measured value between 1 and 2, a value such as 1.7765 can be measured. The noise is introduced by applying the bias voltage to the sensor by use of PWM systems and RC networks 270 coupled to an OPAMP 210 which is in turn is coupled to the sensor.

To achieve long operational lifetime of the device, while maintaining high performance in the SoC 230, the overall average power consumption is reduced. Various embodiments can achieve this as a result of the bias voltage generation provided to the sensor 240 produced by the added RC and ADC subsystem(s) 270. The use of a PWM system and RC networks 220 to apply the bias voltage to the sensor 240 via a low power OPAMP 210, allows for the voltage generator to be halted and SoC 230 to be allowed to enter a low power state during periods between measurements. While these periods are not necessarily large, the effect can be great, as the key factor is the ratio between on and off time. By allowing the SoC 230 to be in extremely low power mode during portions of the operating time when a sample is not required, it allows the bias voltage to continue the electrochemical reaction while the SoC 230 is in low power mode thus optimizing the ratio of on to off time for the SoC 230. Since the SoC 230 operation is the dominant source of power consumption in the system, it is clear that it must be well managed. By using a high quality OPAMP 210, which has a low bias current and characteristically high input impedance, the system can maintain a very accurate bias voltage while in low power mode by using the capacitors in the RC networks 220 coupled to the PWM system. This allows the PWM system to be turned off for long periods of time which allows the system to measure the electrochemical values periodically with high accuracy.

What is claimed is:

1. A method for providing a variable reference voltage to an input of an operational amplifier, comprising:
   calculating a PWM/PDM signal to generate a target reference voltage using an RC network;
   connecting a PWM/PDM generator to the RC network and applying the calculated PWM/PDM signal to generate a reference voltage;
   waiting for the reference voltage to settle;

measuring the reference voltage and comparing the measured voltage to the target reference voltage;

adjusting the PWM/PDM signal until a measured voltage of the reference voltage is at the target reference voltage;

turning off and disconnecting the PWM/PDM generator from the RC network; and waiting a period of time in a low power state.

2. The method according to claim 1, wherein the adjusting step includes increasing or decreasing the number of bits for the PWM/PDM signal.

3. The method according to claim 1, further including the step of sampling an output of the op amp during the low-power wait time.

4. The method according to claim 1, further comprising the steps of:

inducing pseudorandom noise on the reference voltage during a sample period;

taking multiple sample measurements of an output of the op amp during the sample period; and averaging the multiple samples to reduce ADC quantization error.

5. The method according to claim 4, wherein the pseudorandom noise is generated by the first RC network or the second RC network.

6. A method for providing a variable reference voltage to an input of an operational amplifier, comprising:

calculating a first PWM/PDM signal to generate a target reference voltage using a first RC network;

connecting a first PWM/PDM generator to the first RC network and applying the first calculated PWM/PDM signal to generate a reference voltage;

waiting a time period that is at least X times the time constant of the first RC network, where X is 3 or greater;

turning off the first PWM/PDM generator and disconnecting it from the first RC network;

turning on a second PWM/PDM generator and connecting it to a second RC network to adjust or maintain the reference voltage, the second RC network having a time constant at least Y times the time constant of the first RC network, where Y is 5 or greater, waiting a time period that is at least Z times the time constant of the second RC network, where Z is 0.5 or greater, turning off the second PWM/PDM generator and disconnecting it from the second RC network; and waiting a period of time in a low power state.

7. The method according to claim 6, further comprising:

using the first PWM/PDM signal to quickly settle the reference voltage to the target value; and using the second PWM/PDM signal to maintain and fine tune the reference voltage to the target value.

8. The method according to claim 6, wherein X is 10, Y is 10 and Z is 1.

9. The method according to claim 6, further comprising the steps of:

inducing pseudorandom noise on the reference voltage during a sample period;

taking multiple sample measurements of an output of the op amp during the sample period; and averaging the multiple samples to reduce ADC quantization error.

10. The method according to claim 9, wherein the pseudorandom noise is generated by the first RC network or the second RC network.

* * * * *